United States Patent
Vayser et al.

(10) Patent No.: US 9,229,165 B2
(45) Date of Patent: *Jan. 5, 2016

(54) MICRO-OPTIC ADAPTERS AND TIPS FOR SURGICAL ILLUMINATION FIBERS

(71) Applicant: Invuity, Inc., San Francisco, CA (US)

(72) Inventors: Alex Vayser, Mission Viejo, CA (US); Kenneth B. Trauner, San Francisco, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,910

(22) Filed: Oct. 25, 2013

(65) Prior Publication Data

US 2014/0049979 A1    Feb. 20, 2014

Related U.S. Application Data

(63) Continuation of application No. 13/605,891, filed on Sep. 6, 2012, now Pat. No. 8,594,472, which is a continuation of application No. 12/349,358, filed on Jan. 6, 2009, now Pat. No. 8,285,093, which is a (Continued)

(51) Int. Cl.
*G02B 6/00*    (2006.01)
*G02B 6/26*    (2006.01)
(Continued)

(52) U.S. Cl.
CPC . *G02B 6/241* (2013.01); *A61B 1/07* (2013.01); *G02B 6/262* (2013.01); *G02B 6/34* (2013.01);
(Continued)

(58) Field of Classification Search
CPC ............ G02B 6/26; G02B 6/262; G02B 6/27; A61B 1/06; A61B 1/0646; A61B 1/0676; A61B 1/07

USPC .......... 385/11, 15, 27, 31, 36, 37, 39, 43, 50, 385/51, 53, 115, 901, 902; 359/485.01; 600/249

See application file for complete search history.

(56) References Cited

U.S. PATENT DOCUMENTS 3,638,644 A    2/1972    Reick
3,641,332 A    2/1972    Reick et al.
(Continued)

FOREIGN PATENT DOCUMENTS

EP    0101781 A1    3/1984
EP    0450149 A1    10/1991
GB    2078526 A    1/1982

OTHER PUBLICATIONS

European search report dated Oct. 22, 2012 for EP Application No. 07776430.6.

(Continued)

*Primary Examiner* — Akm Enayet Ullah
*Assistant Examiner* — Michael Mooney
(74) *Attorney, Agent, or Firm* — Wilson Sonsini Goodrich & Rosati

(57) ABSTRACT

A microstructure optical adapter or tip according to the present disclosure may incorporate precision micro structure optical components engaging the input or output end of light energy delivery devices for customized light delivery of the light energy. The incorporation of precision micro structure optical components in injection molded plastic or glass parts will allow for inexpensive modification of the output light while also serving to protect the end of the illumination device. The micro structure optical components may also be incorporated in an adapter to tailor the light energy to the subsequent device.

17 Claims, 3 Drawing Sheets

Related U.S. Application Data continuation of application No. 11/796,498, filed on Apr. 26, 2007, now Pat. No. 7,474,820.

(60) Provisional application No. 60/795,986, filed on Apr. 27, 2006.

(51) Int. Cl.
*G02B 6/04* (2006.01)
*A61B 1/06* (2006.01)
*G02B 6/24* (2006.01)
*G02B 6/34* (2006.01)
*A61B 1/07* (2006.01)
*A61B 18/22* (2006.01)
*G02B 6/32* (2006.01)

(52) U.S. Cl.
CPC ............ *A61B 2018/2261* (2013.01); *G02B 6/32* (2013.01); *Y10S 385/901* (2013.01); *Y10S 385/902* (2013.01)

(56) References Cited

U.S. PATENT DOCUMENTS

| | | | |
|---|---|---|---|
| 3,890,960 A | 6/1975 | Wunsch et al. | |
| 4,226,228 A | 10/1980 | Shin et al. | |
| 4,562,832 A | 1/1986 | Wilder et al. | |
| 4,592,344 A | 6/1986 | Scheer | |
| 4,597,030 A | 6/1986 | Brody et al. | |
| 4,605,990 A | 8/1986 | Wilder et al. | |
| 4,617,467 A * | 10/1986 | Senftle et al. | 250/461.1 |
| 4,643,172 A | 2/1987 | Taff et al. | |
| 4,697,578 A | 10/1987 | Burgin | |
| 4,807,599 A | 2/1989 | Robinson et al. | |
| 4,842,356 A | 6/1989 | Mori | |
| 4,909,587 A * | 3/1990 | Okamoto et al. | 385/37 |
| 4,961,617 A | 10/1990 | Shahidi et al. | |
| 5,035,232 A | 7/1991 | Lutze et al. | |
| 5,106,387 A | 4/1992 | Kittrell et al. | |
| 5,117,433 A * | 5/1992 | Tatsuno et al. | 372/22 |
| 5,185,836 A | 2/1993 | Baker | |
| 5,269,777 A | 12/1993 | Doiron et al. | |
| 5,321,258 A | 6/1994 | Kinney | |
| 5,353,786 A | 10/1994 | Wilk et al. | |
| 5,479,543 A | 12/1995 | Black | |
| 5,640,961 A | 6/1997 | Verdonk | |
| 6,185,356 B1 | 2/2001 | Parker et al. | |
| 6,243,215 B1 * | 6/2001 | Hirota et al. | 359/742 |
| 6,268,960 B1 * | 7/2001 | Hirota et al. | 359/460 |
| 6,504,985 B2 | 1/2003 | Parker et al. | |
| 6,845,193 B2 | 1/2005 | Loeb et al. | |
| 7,068,883 B2 | 6/2006 | Ludington et al. | |
| 7,113,336 B2 | 9/2006 | Crosby | |
| 7,306,559 B2 | 12/2007 | Williams | |
| 7,373,028 B2 | 5/2008 | He et al. | |
| 7,474,820 B2 | 1/2009 | Vayser et al. | |
| 8,285,093 B2 | 10/2012 | Vayser et al. | |
| 2002/0141006 A1 * | 10/2002 | Pocius et al. | 359/15 |
| 2003/0004412 A1 | 1/2003 | Izatt et al. | |
| 2003/0091278 A1 * | 5/2003 | Schaschek | 385/33 |
| 2003/0165026 A1 * | 9/2003 | Meyers et al. | 359/873 |
| 2005/0112884 A1 * | 5/2005 | Gormley | 438/689 |
| 2006/0150893 A1 | 7/2006 | Uchida et al. | |
| 2007/0014516 A1 | 1/2007 | Sato | |
| 2012/0330107 A1 | 12/2012 | Vayser et al. | |

OTHER PUBLICATIONS

International search report and written opinion dated Aug. 6, 2008 for PCT/US2007/010355.
Office action dated Jan. 9, 2013 for U.S. Appl. No. 13/605,891.
Office action dated Jan. 11, 2008 for U.S. Appl. No. 11/796,498.
Office action dated Feb. 24, 2011 for U.S. Appl. No. 12/349,358.
Office action dated Jun. 21, 2011 for U.S. Appl. No. 12/349,358.
Office action dated Sep. 7, 2010 for U.S. Appl. No. 12/349,358.
Office action dated Nov. 8, 2011 for U.S. Appl. No. 12/349,358.
Office action dated Dec. 10, 2009 for U.S. Appl. No. 12/349,358.

* cited by examiner

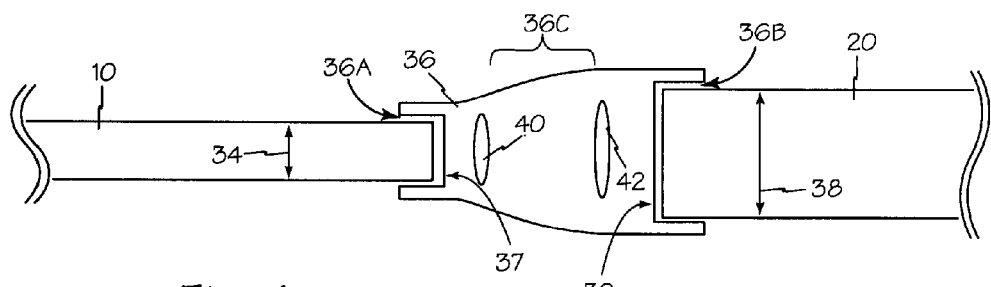
Fig. 4
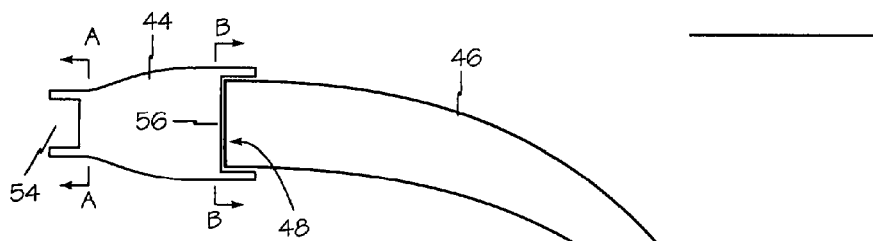
Fig. 5
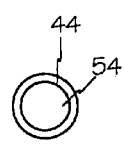
Fig. 6
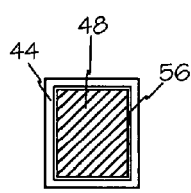
Fig. 7
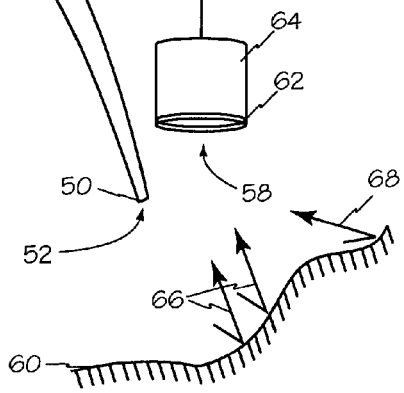

MICRO-OPTIC ADAPTERS AND TIPS FOR SURGICAL ILLUMINATION FIBERS

CROSS-REFERENCE

The present application is a continuation of U.S. patent application Ser. No. 13/605,891 now U.S. Pat. No. 8,594,472 filed Sep. 6, 2012, which is a continuation of U.S. patent application Ser. No. 12/349,358 now U.S. Pat. No. 8,285,093 filed Jan. 6, 2009, which is a continuation of U.S. patent application Ser. No. 11/796,498 now U.S. Pat. No. 7,474,820 filed Apr. 26, 2007, which is a non-provisional of, and claims the benefit of U.S. Provisional Application No. 60/795,986 filed Apr. 27, 2006; the entire contents of each of which is incorporated herein by reference.

FIELD OF THE INVENTIONS

The inventions described below relate to the field of surgical illumination and more specifically to Micro Structured Optical adapters and end caps for surgical illumination.

BACKGROUND OF THE INVENTION

Illumination devices, such as fiber optics, have many applications and generally employ conventional methods such as reflective surfaces or total internal reflection to deflect or focus the light energy. Some devices also have modifications of the distal end or tip geometry to generate focused or defocused beams. Tip modifications for optical fibers are typically produced by polishing or grinding of the fiber tip or the end of a bundle of fibers. Conventional techniques have also included use of high temperatures such as with use of a fusion splicer to create ball tip structures generated by melting the core of an optical fiber.

The limitation of these techniques is that they require accurate manipulation of the device resulting in a modified section which is then left unprotected. For optical fibers, the techniques for polishing or manipulating the tip are costly, time consuming and result in a fragile end product. The techniques available for creating lensing surfaces using the device itself are limited and generate limited optical output lensing options.

Illumination devices such as laser fibers for medical use are frequently used either in direct contact with tissue or in a fluid medium. In these settings, focus of the laser beam emanating from the fiber is difficult to control due to the similar indices of refraction of the various media and the fiber.

What is needed is a versatile technique for terminating illumination devices, or for adapting illumination devices to optimize the light energy and provide desired optical performance.

SUMMARY OF THE INVENTION

A micro structured optical adapter or tip according to the present disclosure may incorporate optical lensing structures to be placed over the end of any suitable illumination device such as fiber optic laser delivery devices. The cap or adapter may incorporate micro structured optical components such as for example gratings, prisms and or diffusers to operate as precision optics for customized delivery of the light energy. These components may be formed as injection molded plastic or glass parts to allow for inexpensive modification of the output light and also serve to protect the end of the device, such as a cleaved fiber optic bundle. The micro structured optical components may also be incorporated in an adapter to tailor the light energy to the subsequent devices. The micro structured optical components may also be used to polarize and/or filter the light energy entering or exiting the illumination device.

BRIEF DESCRIPTION OF THE DRAWINGS

FIG. 4 is a cutaway view of a micro structure optical adapter according to the present disclosure.

FIG. 5 is a cutaway view of a micro structure optical adapter and end element according to the present disclosure.

FIG. 6 is a cross section view of the micro structure optical adapter of FIG. 5 taken along A-A.

FIG. 7 is a cross section view of the micro structure optical adapter of FIG. 5 taken along B-B.

DETAILED DESCRIPTION OF THE INVENTION

Figure 1:
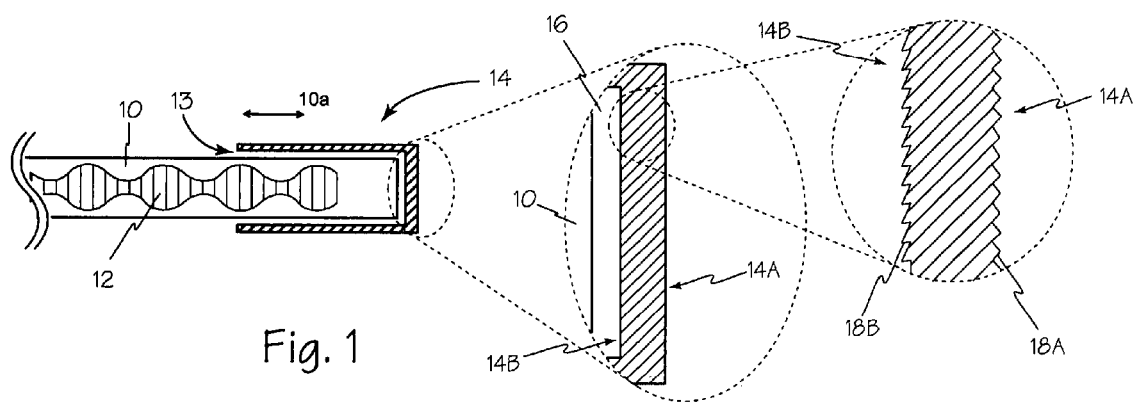
FIG. 1 is a cutaway view of a laser fiber and micro structure optical end cap according to the present disclosure.

In FIG. 1 medical illumination fiber 10 engages an end cap such as cap 14 to form an optical path with one or more micro structure optical surfaces such as inner optical surface 14A or outer optical surface 14B and or one or more air gaps such as gap 16 and or index matching material to control light 12. Any suitable surface such as inner an outer optical surfaces 14A and 14B or a portion of an inner or outer surface may be formed to include micro structure optical structures such as structure 18A and or 18B thereon. Cap 14 may be made of glass, plastic or any other suitable material and may be sized to enable bore 13 to frictionally engage optical fiber 10.

Input and or output micro optical structures such as structure 18A or structure 18B may adopt any suitable configuration to accomplish one or more of the functions of diffracting, deflecting, refracting or polarizing light passing through the micro structure optical component. Such structures individually or in combination may be used to adjust the intensity and or the phase of the light energy similar to holographic film which may also be used.

Figure 2:
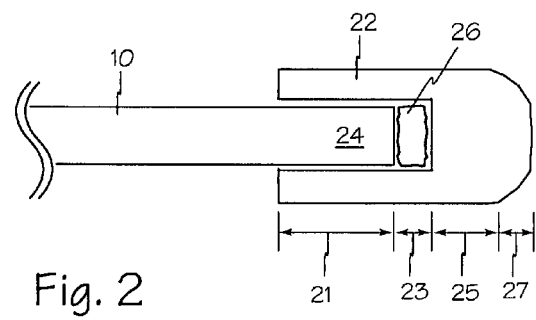
FIG. 2 is a cutaway view of an alternate micro structure optical end cap according to the present disclosure.

Referring now to FIG. 2 illumination fiber 10 includes a light management cap such as cap 22 engaging end 24 of fiber 10. A light management cap according to the present disclosure such as cap 22 may engage a fiber along engagement zone 21 mechanically, frictionally, or using adhesives or any other suitable technique. Matching zone 23 of cap 22 may be an air gap, or be filled with any suitable material such as adapter material 26 to achieve a suitable index transition between illumination fiber 10 and cap 22. Body zone 25 of cap 22 may be composed of solid cap material, or any suitable combination of air gaps or inserted components may also be used. Cap zone or output zone 27 may be formed in any suitable shape and may include microstructure such as structures 18A and 18B to achieve desired output light management.

Figure 3:
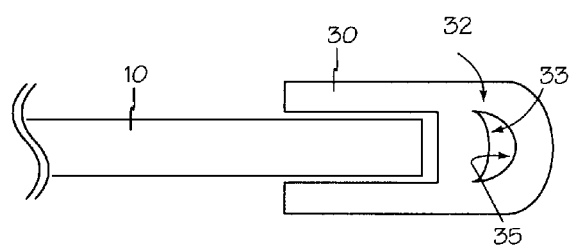
FIG. 3 is a cutaway view of another alternate micro structure optical end cap according to the present disclosure.

Referring to FIG. 3, light management cap 30 may include one or more chambers or other inserted structures to control light emanating from illumination fiber 10. Chamber 32 may be filled with air or other suitable material to achieve the desired light management. Incident surface 33 and outlet surface 35 of chamber 32 may be formed to have any suitable surface characteristics such as surfaces 18A and 18B.

Referring now to FIG. 4, fiber adapter 36 includes an input bore 36A and an output bore 36B. Input bore 36A may adopt any suitable geometry to engage a first element such as illumination fiber 10 having a dimension 34 and couple it to a second element such as fiber 20 having a dimension 38. Dimensions 34 and 38 may be the same or different. Surfaces 37 and 39 may be formed to have any suitable surface characteristics such as micro structure optical surfaces 18A and 18B. A fiber adapter such as adapter 36 may also include one or more energy conforming elements such as elements 40 and 42. Elements 40 and 42 may be solid or hollow with one or more surfaces including conventional shapes and or micro structure optical components. Adapters such as adapter 36 may also be used to connect an illumination fiber to an end element having any suitable dimensions and geometry. End elements may have round, oval, rectangular, and polygonal or any other suitable cross section. Adapters such as adapter 36 may also incorporate a flexible center section or light conduit such as center section 36C, thereby allowing element 20 to be oriented in any position relative to illumination fiber 10. This allows element 20 to be oriented in a selected direction to accommodate selected use or selected mounting on auxiliary equipment. Center section 36c may be fabricated from optical fibers, silicone or other suitable flexible material. Elements 40 and 42 may serve to couple light into and out of this flexible section, for example, as suitably designed lenses.

Flexible adapter 36 may be constructed entirely of flexible material, for example, injection molded silicone, or it may be fabricated as an assembly including an input connector, flexible light conduit, and output connector using suitable fabrication and assembly techniques. A flexible adapter may be incorporated as a permanent component of an illumination input, for example as part of a fiber optic light guide cable using adhesive or other suitable joining technique, thereby allowing end elements to be changed without fear of disengaging the adapter from the illumination input. Conversely, a flexible adapter may be incorporated as a permanent component of an end element or illumination device using suitable joining techniques, thereby allowing different end element devices to be used with the same illumination input without fear of disengaging the adapter or without the added step of replacing an adapter for each new device to be used.

Referring to FIG. 5, FIG. 6 and FIG. 7 adapter 44 engages a generally round illumination fiber at receptacle 54. Receptacle 56 engages device 46 having a generally rectangular cross-section. As discussed above surface 48 of device 46 may incorporate suitable micro structure optical components to enhance light coupling into device 46. Facets such as facet 50 may also incorporate micro structure optical components or other coatings such as polarizing coating 52. Adapter 44 may also include a flexible middle portion that conducts light, thereby allowing device 46 to be oriented in any direction relative to an illumination input at receptacle 54.

Polarized coating 52 emits polarized light to optimize viewing of site 60. Use of a complementary polarization microstructure or coating such as microstructure 58 on lens 62 permits any suitable light receiver such as camera 64 to receive only properly polarized light 66 and reject other reflected light such as light 68 thus minimizing distracting reflections and glare.

Figure 8:
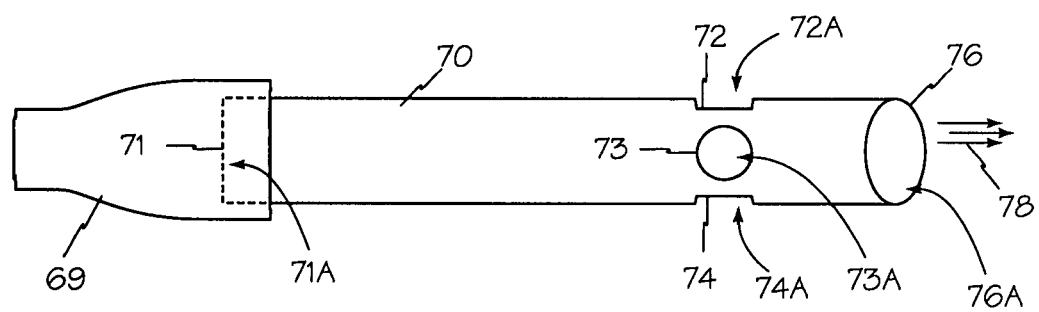
FIG. 8 is a side view of a micro structure optical adapter and an end element according to the present disclosure.

Referring now to FIG. 8, adapter 69 is coupled to end element 70. End element 70 may include one or more light emission facets such as facets 72, 73, 74 and 76 for output of light energy. Input surface 71 of end element 70 may incorporate polarizing microstructure 71A. Each light emission facet may have a polarizing microstructure or coating such as microstructures 72A, 73A, 74A and 76A, and two or more of the light emission facets may have similarly oriented polarization. Controlling the orientation of a polarized input may allow light to be emitted from one or more facets having complimentary polarization. For example, adapter 69 may be made to rotate relative to end element 70 such that this rotation causes separate polarizing structures formed in adapter 69 to line up with at least part of input surface 71, without polarizing microstructure 71A, such that light emits from complementary polarization facet 72 at zero degrees of relative rotation of adapter 69, but that light emits from separate complimentary polarization facet 74 at 90 degrees of relative rotation of adapter 69.

End element 70 or any adapter or end cap may also be formed to include one or more constituent elements to cause end element 70 to filter and or polarize the light energy input into end element 70 and cause emitted light 78 to have a desired frequency or combination of frequencies and or polarization orientation. End element 70 may also be treated to cause its constituent element or elements to operate as a light filter enabling chromatography. End element 70 may include co-molded element 73 that splits the incoming light such that a fraction of the light exits facet 72, which may have a filtering microstructure or coating 72A, a fraction exits facet 74 incorporating redirecting microstructure prism 74A, and a fraction exits normally through facet 76.

A micro structured optical cap may also contain one or more gas or air filled chambers that allows the light to refract prior to reaching the tissue or fluid. A cap or adapter may also operate as a filter to pass a desired frequency or frequencies of light by selecting the gas filling and or additives to be incorporated with the material of the cap or adapter.

A micro structured optical adapter or tip according to the present disclosure may use micro structured optical components to manage or adapt the light output of an illumination fiber. By making a device or adapter consisting of one or more micro structured optical components injection molded onto a flat window, which can be attached to a standard fiber, the light output of the illumination fiber may be controlled without the need to polish the tip of the fiber.

In another aspect, one or more surfaces in the optical path of an adapter or cap may include a predetermined micro structured optical components. Different optical light output shapes may be achieved by creating specific microstructure surfaces or patterns.

It is also possible to apply the microstructure technology to deflect light as well as focus it into a particular shape. Microstructures may be applied to the back and or the front of a refractive element to deflect the beam as well as shape it. Microstructure surfaces may also be combined with one or more air gaps and or conventional surface shaping to achieve desired optical performance.

Other potential configurations can be designed to engage and secure the caps to the end of a fiber. This can be done using adhesive with index matching glue, or it could be done mechanically leaving an air space. The cap could be made from glass or plastic, or other suitable optical material.

A micro structure optical adapter according to the present disclosure may be used to adapt any suitable illumination energy from a conventional round source such as an optical fiber or fiber bundle to an end element having any suitable cross section. This adapter may be flexible, allowing the user to preferably orient the end element relative to the source. The use of micro structure optical components and or conventional diffraction and or refraction elements may permit optimal transfer of light energy from the fiber to the end element. These structures can be part of an injection mold or may be applied as a separate film.

In a still further aspect of the present disclosure one or more surfaces in an illumination path may be polarized using any suitable technique such as an injection molded micro structure optical component, thin film coating or other. Use of polarized light in a surgical environment may provide superior illumination and coupled with the use of complementary crossed polarized material on viewing devices such as video or still cameras, surgical loupes, microscopes, face shields or surgeons glasses may reduce reflected glare providing less visual distortion and more accurate color resolution of the surgical site.

Due to an expensive and complex process, standard fiber optic bundles do not preserve polarization. Therefore, polarized light that is transmitted through a fiber optic bundle will become depolarized. The application of a tip device with polarization structures would still allow polarized light to be delivered.

In a still further aspect of the present disclosure use of a micro structure optical tip or adapter incorporating filtering additives such as dyes or structures such as for example diffraction gratings, may produce light of a selected frequency. The frequency of the light output may be selected to provide selective reflection and or absorption to enhance surgery, therapy and or diagnosis.

While polarizing and filtering components may be fabricated in adapters and or tips that are subsequently applied to an illumination device, another further aspect of this disclosure is the fabrication of these components directly in the illumination device. As noted, optical fibers are very difficult to modify to form these components, but modern tooling and injection molding processes provide that capability, for example, with plastic waveguides or light pipes. Facets may be formed in an injection molded illumination device wherein the facet face, which may normally act as a refraction surface, may be modified to include micro structure optical components that perform polarization and or filtering functions. For example, such structures may be molded into the input face to polarize light as it enters the illumination device so that the light exiting the device is polarized.

Furthermore, micro structure optical components may also be formed of metal or other suitable materials, e.g., beam splitters or polarization grids, then co-molded into a plastic illumination device. For example, a beam splitter co-molded in the center of a plastic light pipe may force part of an incoming light beam out of a facet with a green filter grating molded in and part of the light beam out of a second facet with a red filter grating molded in. The user may simply reposition the light pipe to use either color light for a particular purpose.

In typical application, an adapter may be disposed between a light source, such as a fiber optic light guide cable, and an end element illumination device, such as a fiber optic light pipe or a plastic waveguide or light pipe. A tip may be used instead of the adapter for certain functions, for example, providing a polarizing tip to a standard fiber optic light pipe. The user may remove and replace adaptors and tips as needed for specific light output needs, but the process of removing and replacing adapters and tips may be troublesome, for example, during a surgical procedure.

In another further embodiment, a polarization rotator such as a half-wave plate which can rotate polarized light by a predetermined angle may provide different angles of polarization to be combined with matching polarized facets on an end element device or polarized sections in a tip. Each facet or section might be directed in different visual angles or may have a filtering film applied. As the polarization rotator is adjusted to a particular polarizing angle, polarized light travels down the end element to the facet or tip section that has a matching polarization. Light then exits from this matched output facet or section, but not other facets or sections due to the polarization effect. This may be used to selectively illuminate certain areas of a visual field or to select certain filters for better visualization of elements in a visual field. For example, in a surgical procedure, the adjustable polarizer could be adjusted so that light only shines out of a tip section that provides filtered light suitable for visualization of blood vessels, while a different setting on the adjustable polarizer causes light to shine out of a separate tip section that provides a different color of light suitable for visualization of nerves.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method for illuminating a work area, said method comprising:
   providing an optical fiber, and an optical tip having a bore and an output zone with a plurality of microstructures comprising a plurality of prisms, the prisms configured to refract light passing therethrough and direct the light away from the optical tip, wherein the optical tip has an inner optical surface and an outer optical surface, and wherein the plurality of microstructures are disposed on the outer optical surface and the inner optical surface;
   disposing the optical fiber in the bore;
   passing the light from the optical fiber through the optical tip; and
   directing the light through the output zone and away from the optical tip toward the work area.

2. The method of claim 1, further comprising diffracting, reflecting, or polarizing the light passing through the plurality of microstructures.

3. The method of claim 1, further comprising providing a matching zone disposed between the optical fiber and the optical tip, wherein the matching zone matches optical characteristics between the optical fiber and the optical tip.

4. The method of claim 3, wherein the optical fiber has an index of refraction and the optical tip has an index of refraction, and wherein the matching zone matches the index of refraction of the optical fiber with the index of refraction of the optical tip.

5. The method of claim 3, wherein providing the matching zone comprises forming an air gap between the optical fiber and the optical tip.

6. The method of claim 3, wherein providing the matching zone comprises disposing an index matching material between the optical fiber and the optical tip, wherein the index matching material provides an index of refraction transition between the optical fiber and the optical tip.

7. The method of claim 1, further comprising adhesively securing the optical fiber to the optical tip.

8. The method of claim 1, further comprising mechanically securing the optical tip with the optical fiber.

9. The method of claim 1, further comprising frictionally engaging the optical tip with the optical fiber.

10. The method of claim 1, wherein disposing the optical fiber in the bore comprises removably coupling the optical fiber with the bore.

11. The method of claim 1, further comprising optically coupling a light source with the optical fiber.

12. The method of claim 1, wherein the work area is a surgical field.

13. The method of claim 1, further comprising coupling the optical tip with a second optical element, and wherein the light is directed from the optical tip to the second optical element toward the work area.

14. The method of claim 1, wherein the optical tip is flexible and the method further comprises orienting the optical tip in a selected direction.

15. The method of claim 1, wherein directing the light comprises directing the light through a distal portion of the optical tip.

16. The method of claim 1, wherein the optical fiber comprises a fiber bundle.

17. The method of claim 1, wherein the plurality of microstructures comprise gratings or diffusers.

* * * * *